United States Patent [19]

Herman

[11] Patent Number: Plant 5,649

[45] Date of Patent: Jan. 28, 1986

[54] *OLEA EUROPAEA* CV. MONHER

[75] Inventor: Julian Herman, Irvine, Calif.

[73] Assignee: Monrovia Nursery Company, Azusa, Calif.

[21] Appl. No.: 633,359

[22] Filed: Jul. 23, 1984

[51] Int. Cl.[4] ..... A01H 5/00
[52] U.S. Cl. ..... Plt./33
[58] Field of Search ..... Plt./33

*Primary Examiner*—Robert E. Bagwill

[57] ABSTRACT

A new and distinct selection of *Olea europaea* Linnaeus (popularly known as an Olive tree) which hereinafter shall be referred to as *Olea europaea* cultivar Monher. *Olea europaea* cv. Monher differs from other selections of *Olea europaea* by possessing unique combinations of more corolla lobes per flower, a lighter green color of foliage, foliage which is longer, more narrow and thinner in texture, and a finer textured appearance to the overall habit of the tree and lack of fruit.

2 Drawing Figures

DISCOVERY

This invention relates to a new and distinct selection of *Olea europaea,* a member of the Olive family, Oleaceae. *Olea europaea* cv. Monher was discovered by me at Irvine Wholesale Nursery, Irvine, Calif. as a sport of *Olea europaea* in 1978.

The plant to date is known to exist only within the boundaries of Irvine Wholesale Nursery, 45 Windjammer, Irvine, Calif. and Monrovia Nursery, 18331 E. Foothill Blvd., Azusa, Calif. This selection has not been offered for sale or described in any publication.

REPRODUCTION

This new and distinct selection has been strictly asexually reproduced by cuttings and grafting at Monrovia Nursery. Sexual reproduction, such as speed propagation has not been attempted as no fruit or seed has formed from this plant.

BRIEF DESCRIPTION OF THE DRAWINGS

The above photo, FIG. 1 labeled selection shows the inventor with a specimen of the selected plant exhibiting the overall habit and appearance.

The photo below, FIG. 2 designated prior art and selection displays a foliage sample. My selection exhibits narrower and longer foliage and lack of fruit.

CHARACTERISTICS

*Olea europaea* cv. Monher differs from the commonly grown *Olea europaea* cv. Manzanillo as listed below:

1. The new selection has more corolla lobes ranging from 4 to 6 with 5 an average number. *Olea europaea* cv. Manzanillo has corolla lobes strictly in fours, the numbers do not vary.

2. The new selection has a lighter green foliage, Spinach Green 0960. The cv. Manzanillo is a darker green, Ivy Green 0001060/1 (from British Horticultural Color Chart).

3. My new selection has foliage which is longer ranging from 5.5 to 7.6 cm. Cultivar Manzanillo does not have foliage longer than 5 cm.

4. The foliage on cultivar Manzanillo is wider and not as narrow as in my selection. This narrower, longer foliage gives my selection a fine textured appearance to its overall growth habit.

5. My selection does not produce fruit. The cultivar Manzanillo produces fruit.

My new selection differs from U.S. Plant Pat. No. 4,464 as listed below:

1. The foliage of my selection is longer ranging from 5.5 to 7.6 cm. The U.S. Plant Pat. No. 4,464 ranges from 4.5 cm to 5 cm in length.

2. The foliage of my selection is lighter, a Spinach Green 0960. The U.S. Plant Pat. No. 4,464 is darker 0001060/3 Ivy Green.

My new selection differs from U.S. Plant Pat. No. 3,197 as below:

1. My new selection has a lighter upper leaf surface 0960, Spinach Green. U.S. Plant Pat. No. 3,197 has a much darker leaf surface, Ivy Green 0001060.

2. My new selection has a more narrow leaf, the widest measuring 1.5 cm. U.S. Plant Pat. No. 3,197 is much broader measuring 1.7 to 2.2 cm.

DESCRIPTION

Below is a detailed description of the new selection, all color terminology is derived from The British Horticultural Color Charts.

Overall size habit:

The mature tree size is approximately 22 feet in height and approximately 15 feet in width.

Foliage:

- *Shape.*—Elliptic.
- *Base.*—Narrow cuneate.
- *Tip.*—Small mucronate tip.
- *Margins.*—Entire.
- *Width.*—1.1–1.5 cm.
- *Length.*—5.5–7.6 cm.
- *Arrangement.*—Opposite and alternate.
- *Petiole.*—3 to 5 mm in length.
- *Color.*—Upper leaf surface: Spinach Green 0960. Lower leaf surface: Silvery.

Flower:

- *Diameter.*—5 mm.
- *Corolla lobes.*—Vary from 4 to 6 with 5 the average number.
- *Corolla lobe length.*—3 mm. Width: 1–1.5 mm.
- *Peduncle.*—6 to 8 mm in length.
- *Buds.*—2 mm length and width.
- *Color.*—Creamy white.
- *Calyx.*—Slightly lobed 4–6.

I claim:

1. A new and distinct selection of *Olea europaea* as substantially shown and described herein, characterized particularly as to novelty by the unique combination of more corolla lobes per flower, a lighter green color of foliage, foliage which is longer, more narrow and thinner in texture and a finer and more open appearance to the overall habit of the tree and lack of fruit.

* * * * *

FIG. 1
SELECTION
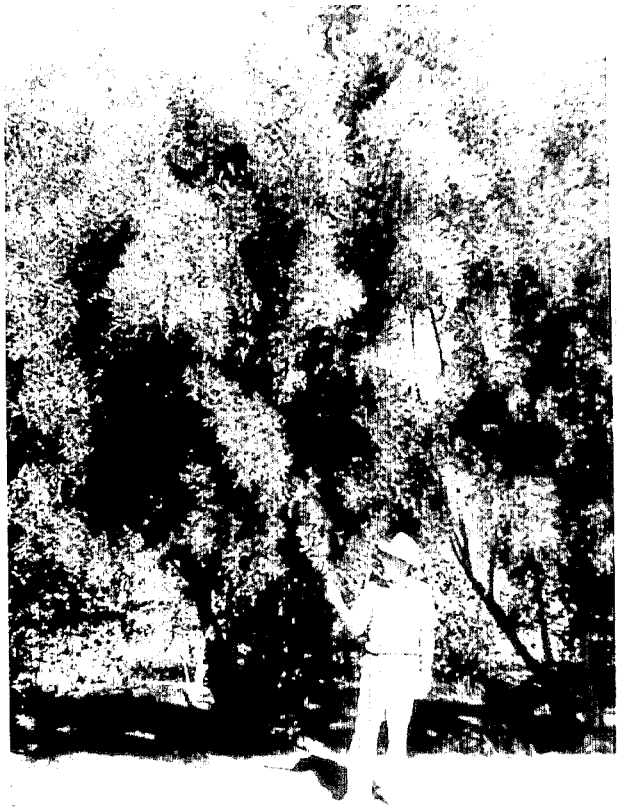
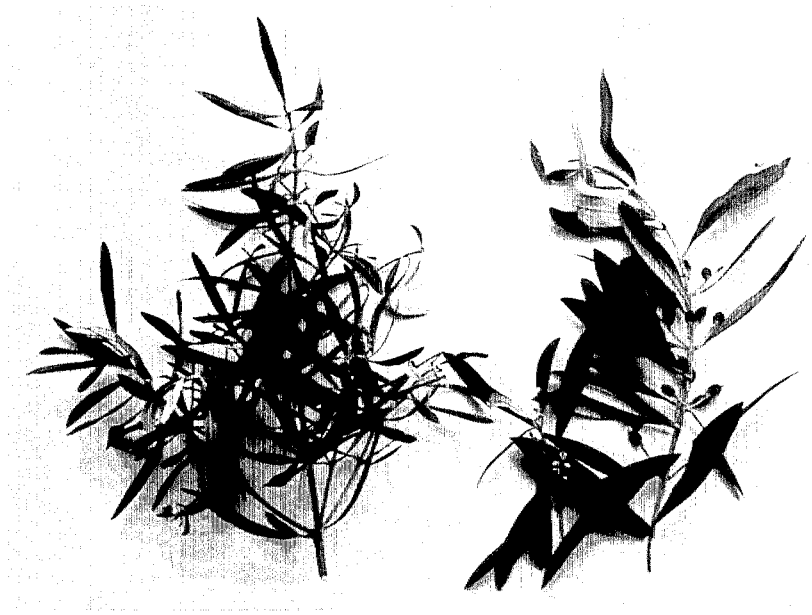
FIG. 2
PRIOR ART (right)
SELECTION (left)